United States Patent
Jiao et al.

(12) 
(10) Patent No.: US 6,403,862 B1
(45) Date of Patent: Jun. 11, 2002

(54) SEED-PREFERRED PROMOTER FROM MAIZE

(75) Inventors: Shuping Jiao, Johnston; Jeffrey E. Habben, Urbandale; Xiaomu Niu, Johnston, all of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/666,179

(22) Filed: Sep. 21, 2000

Related U.S. Application Data

(60) Provisional application No. 60/155,859, filed on Sep. 24, 1999.

(51) Int. Cl.$^7$ .......................... C12N 15/63; C12N 15/82; C07H 21/04; A01H 1/00; A01H 5/00
(52) U.S. Cl. .................. 800/287; 800/298; 536/24.1; 435/320.1; 435/419; 435/468
(58) Field of Search .................................. 800/298, 287; 536/24.1; 435/320.1, 468, 419

(56) References Cited

U.S. PATENT DOCUMENTS

| | | |
|---|---|---|
| 5,623,067 A | 4/1997 | Vandekerckhove et al. |
| 5,767,363 A | 6/1998 | De Silva, et al. |
| 5,824,863 A | 10/1998 | Miki, et al. |

FOREIGN PATENT DOCUMENTS

| | | | |
|---|---|---|---|
| WO | WO 99/37795 | 7/1999 | ........... C12N/15/82 |
| WO | WO 99/16890 | 8/1999 | ........... C12N/15/82 |
| WO | WO 99/53067 | 10/1999 | ........... C12N/15/29 |
| WO | WO 00/11177 | 3/2000 | ........... C12N/15/29 |
| WO | WO 00/12733 | 3/2000 | ........... C12N/15/82 |
| WO | WO 00/40710 | 7/2000 | ........... C12N/15/00 |

OTHER PUBLICATIONS

Kim et al, "A 20 nuclotide upstream element is essential for the nopaline synthase (nos) promoter activity", 1994, Plant Molecular Biology, vol. 24 pp 105–117.*

Benfey et al, "The Cauliflower Mosiac Virus 35S Promoter: Combinatorial Regulation of Transcription in Plants", 1990, Science vol. 250, pp 959–966.*

Smith, Laura, et al., "Temporal and Spatial Regulation of a Novel Gene in Barley Embryos", *Plant Molecular Biology*, vol. 2, No. 2, 1998, p. 255–266.

Walbot, V., *GenBank Accession No.* BE055995, "Maize ESTs from various cDNA libraries sequenced at Stanford University" (Jun. 18, 2000).

Busk, P., "Regulatory elements in vivo in the promoter of the abscisic acid responsive gene rab 17 from maize", *Plant Journal* 11(6):1285–1295 (Jun. 1997).

Gallusci, P., "Differences in cell type–specific expression of the gene Opaque 2 in maize and transgenic tobacco", *Mol. Gen. Genet.* 244(4): 391–400 (Aug. 1994).

Grosset, J., "Characterization of a barley gene coding for an alpha–amylase inhibitor subunit (CMd protein) and analysis of its promoter in transgenic tobacco plants and in maize kernels by microprojectile bombardment", *Plant Mol. Biol.* 34:331–338 (May 1997).

Kim, K., "Molecular cloning and characterization of the amylose–extender gene encoding starch branching enzyme IIB in maize", *Plant Molecular Biology* 38:945–956 (1998).

Klemsdal, S., "Primary structure of a novel barley gene differentially expressed in immature aleurone layers", *Mol. Gen. Genet.* vol. 228:9–16 (Aug. 1991).

Kyozuka, J., "Promoter elements required for developmental expression of the maize Adh1 gene in transgenic rice", *Plant Cell* 6(6):799–810 (Jun. 1994).

May, B., "Transposon sequences drive tissue–specific expression of the maize regulatory gene R–s", *Plant Journal* pp. 241–247 (Jan. 1998).

Sidorenko, L., "Characterization of the regulatory elements of the maize P–rr gene by transient expression assays", *Plant Mol. Biol.* 39(1):11–19 (Jan. 1999).

* cited by examiner

*Primary Examiner*—Elizabeth F. McElwain
*Assistant Examiner*—Cynthia Collins
(74) *Attorney, Agent, or Firm*—Pioneer Hi-Bred International, Inc.

(57) ABSTRACT

The present invention provides a composition and method for regulating expression of heterologous nucleotide sequences in a plant. The composition is a novel nucleic acid sequence for a seed-preferred promoter. A method for expressing a heterologous nucleotide sequence in a plant using the promoter sequence is also provided. The method comprises transforming a plant cell to contain a heterologous nucleotide sequence operably linked to the seed-preferred promoter of the present invention and regenerating a stably transformed plant from the transformed plant cell.

17 Claims, No Drawings

SEED-PREFERRED PROMOTER FROM MAIZE

CROSS-REFERENCE TO RELATED APPLICATION

This application claims priority to, and hereby incorporates by reference, provisional patent application 60/155,859, filed Sep. 24, 1999.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably-linked promoter that is functional within the plant host. Choice of the promoter sequence will determine when and where within the plant the heterologous DNA sequence is expressed. Where continuous expression is desired throughout the cells of a plant, constitutive promoters are utilized. In contrast, where gene expression in response to a stimulus is desired, inducible promoters are the regulatory element of choice. Where expression in specific tissues or organs is desired, tissue-preferred promoters are used. That is, these promoters can drive expression in specific tissues or organs. Additional regulatory sequences upstream and/or downstream from the core promoter sequence can be included in expression cassettes of transformation vectors to bring about varying levels of expression of heterologous nucleotide sequences in a transgenic plant. See, for example, U.S. Pat. No. 5,850,018.

Regulatory sequences may also be useful in controlling temporal and/or spatial expression of endogenous DNA. For example, specialized tissues are involved in fertilization and seed development. Identification of promoters which are active in these seed tissues is of interest.

In grain crops of agronomic importance, seed formation is the ultimate goal of plant development. Seeds are harvested for use in food, feed, and industrial products. The quantities and proportions of protein, oil, and starch components in those seeds determine their utility and value.

The timing of seed development is critical. Environmental conditions at any point prior to fertilization through seed maturation may affect the quality and quantity of seed produced. In particular, the first 10 to 12 days after pollination (the lag phase) are critical in maize seed development. Several developmental events during the lag phase are important determinants of the fate of subsequent seed growth and development. (Cheikh, N. et al., *Plant Physiology* 106:45–51 (1994)) Therefore, a means to influence plant development, particularly in response to stress during this phase of growth, is of interest. Identification of a promoter sequence active in tissues of developing seeds exposed to abiotic stresses would be useful.

Specialized plant tissues are central to seed development. Following fertilization, developing seeds become sinks for carbon translocated via the phloem from sites of photosynthesis. However, developing cereal seeds have no direct vascular connections with the plant; instead, a short-distance transport mechanism operates to move the assimilates from the vascular tissues to the endosperm and embryo. For example, in maize, photosynthate enters the seed via the pedicel; in wheat, via the nucellar projection and the aleurone layer. It is possible that this short-distance assimilate pathway between the phloem and the endosperm can operate to regulate the rate of sucrose transport into the grain. (Bewley, J. D., and M. Black. *Seeds: Physiology of Development and Germination*, N.Y., Plenum Press, 1985. pp. 38–39) Therefore, a promoter active in gene expression within these specialized tissues, such as the pedicel, may have significant effects on grain development.

During rapid seed growth, sucrose is unloaded passively from the phloem into the apoplast of the pedicel parenchyma and inverted to hexose sugars by a cell-wall-bound acid invertase. The hydrolysis of sucrose in the apoplast maintains a favorable gradient for continued unloading from the phloem and provides hexoses that are taken up by the basal endosperm cells. It has been shown that seeds induced to abort, in vitro, have only low levels of invertase activity in the pedicel. (Hanft, J. M. et al. (1986) Plant Physiol. 81:503–510)

Water stress to the plant around anthesis often results in seed abortion or restricted development. Studies suggest that sucrose continues to unload from the phloem at low ovary water potential but accumulates in the symplasm and apoplasm of the pedicel because of low invertase activity. (Zinselmeier, C., et al., (1995) Plant Physiol. 107:385–391) This conclusion is supported by the findings of Miller and Chourey (Plant Cell 4: 297–305 (1992)), who showed that developmental failure of miniature-1 seeds of maize was linked to lack of invertase activity in the pedicel tissue during the early stages of seed development.

Other specialized plant tissues are also closely involved in the critical processes of fertilization and seed development. For example, in maize, the carpels, which make up the ovary wall, become the pericarp, a tough, protective outer seed covering. The scutellum, along with the endosperm, is involved in translocation of assimilates to the developing embryo. The aleurone, the surface layer of endosperm cells, develops to serve as a source of enzymes necessary in germination. (Kiesselbach, T. A. *The Structure and Reproduction of Corn*. N.Y., Cold Spring Harbor Press, 1999)

In light of the important contributions of these specialized seed tissues to proper grain development, identification of a promoter sequence affecting gene expression in these tissues would be useful. Further, it would be desirable to identify a promoter sequence active in these specific tissues at appropriate, critical times. Even more desirable would be the identification of a promoter sequence active in these specific tissues at appropriate, critical times, which is not negatively affected by environmental stress to the plant.

The maize Glb1 gene encodes globulin-1, a major embryo storage protein. (Kriz, A. L., et al. (1986) Plant Physiol. 82:1069–1075) Glb1 is expressed in the developing maize seed during embryo development. (Belanger, F. C., et al. (1989) Plant Physiol. 91:636–643) The promoter region of Glb1 has been identified, cloned, and introduced into tobacco plants by Agrobacterium-mediated transformation. (Liu, S., et al. (1996) Plant Cell Reports 16:158–162) The transformed plants demonstrate that the Glb1 promoter has desirable temporal and tissue specificity. However, the Glb1 promoter is positively regulated by abscisic acid (ABA). (Kriz, A. L., et al. (1990) Plant Physiol. 92:538–542; Paiva, R., et al., (1994) Planta 192:332–339) Levels of the plant hormone ABA are known to fluctuate under conditions of cold or desiccation. (Himmelbach, A., et al. (1998) Phil. Trans. R. Soc. Lond. 353:1439–1444) Thus, the activity of the Glb1 promoter can be differentially affected by environmental stress. A need exists for a promoter sequence active in specific seed-related tissues at critical times in seed development and which is not negatively impacted by environmental stresses to the plant. In particular, it is desirable that the promoter activity is not down-regulated by environmental stresses.

SUMMARY OF THE INVENTION

It is an object of the present invention to provide a novel nucleotide sequence for modulating gene expression in a plant.

It is a further object of the present invention to provide an isolated promoter capable of driving transcription in a seed-preferred manner.

It is a further object of the present invention to provide a method of improved control of an endogenous or exogenous product in the seed of a transformed plant.

It is a further object of the present invention to provide a method for effecting useful changes in the phenotype of a seed of a transformed plant.

It is a further object of the present invention to provide a method for producing a novel product in the seed of a transformed plant.

It is a further object of the present invention to provide a method for producing a novel function in the seed of a transformed plant.

It is a further object of the present invention to provide a method for modulating the timing or rate of development of the seed of a transformed plant.

It is a further object of the present invention to provide a method for regulating the accumulation of photosynthetic products in the developing seed of a transformed plant.

It is a further object of the present invention to provide a method for regulating the production of phytohormones involved in seed development.

It is a further object of the present invention to provide a method for regulating the cell cycle machinery of seeds during their development.

Therefore, in one aspect, the present invention relates to an isolated nucleic acid comprising a member selected from the group consisting of:

a) nucleic acids capable of driving expression in the carpel, embryo scutellum, pedicel, pericarp, aleurone, or pedicel-forming region of a developing seed;

b) nucleic acids capable of driving expression in the carpel, embryo scutellum, pedicel, pericarp, aleurone, or pedicel-forming region of a developing seed during critical periods of seed development;

c) nucleic acids capable of driving expression in the carpel, embryo scutellum, pedicel, pericarp, aleurone, or pedicel-forming region of a developing seed during favorable or unfavorable growing conditions;

d) nucleic acids comprising a functional variant or fragment of at least 20 contiguous nucleotides of the sequence set forth in SEQ ID NO 1;

e) the nucleic acid segment set forth in SEQ ID NO 1;

f) nucleic acids that hybridize to any one of a), b), c), or d), under stringent conditions; wherein stringent conditions include: a hybridization at 42° C. in a solution of 50%(w/v) formamide, 6×SSC, 0.5% SDS, 100 ug/ml salmon sperm, washed with 0.5% SDS and 0.1×SSC at 65° C. for 30 minutes and repeated;

g) nucleic acids having at least 65% sequence identity to SEQ ID NO 1 wherein the % sequence identity is based on the entire sequence and is determined by BESTFIT analysis under default parameters, provided that such homologous sequence is not from barley.

In other aspects, the present invention relates to expression cassettes comprising the promoter operably linked to a nucleotide sequence, vectors containing the expression cassette, and plants stably transformed with at least one expression cassette.

In a further aspect, the present invention relates to a method for modulating expression in the seed of a stably transformed plant comprising the steps of (a) transforming a plant cell with an expression cassette comprising the promoter of the present invention operably linked to at least one nucleotide sequence; (b) growing the plant cell under plant growing conditions and (c) regenerating a stably transformed plant from the plant cell wherein said linked nucleotide sequence is expressed in the seed.

DETAILED DESCRIPTION OF THE INVENTION

In accordance with the invention, a nucleotide sequence is provided that allows initiation of transcription in seed. The sequence of the invention comprises transcriptional initiation regions associated with seed formation and seed tissues. Thus, the compositions of the present invention comprise a novel nucleotide sequence for a plant promoter, more particularly a seed-preferred promoter.

By "seed" or "kernel" is intended to include the grain or ripened ovule of a plant, or more broadly, a propagative plant structure. The terms "seed" and "kernel" are used interchangeably herein.

By "seed-preferred" is intended favored expression in the seed, including at least one of embryo, seed or kernel, pericarp, endosperm, nucellus, aleurone, pedicel, and the like.

By "heterologous nucleotide sequence" is intended a sequence that is not naturally occurring with the promoter sequence. While this nucleotide sequence is heterologous to the promoter sequence, it may be homologous (native) or heterologous (foreign) to the plant host.

By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' untranslated region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue such as the seed can be identified, isolated, and used with other core promoters to confirm seed-preferred expression.

The isolated promoter sequence of the present invention can be modified to provide for a range of expression levels of the heterologous nucleotide sequence. Less than the entire promoter region can be utilized and the ability to drive seed-preferred expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels, enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The term "isolated" refers to material, such as a nucleic acid or a protein, which is: (1) substantially or essentially free from components which normally accompany or interact with it as found in its natural environment. The isolated material optionally comprises material not found with the material in its natural environment; or (2) if the material is in its natural environment, the material has been synthetically altered or synthetically produced by deliberate human intervention and/or placed at a different location within the cell. The synthetic alteration or creation of the material can be performed on the material within or apart from its natural state. For example, a naturally-occurring nucleic acid becomes an isolated nucleic acid if it is altered or produced by non-natural, synthetic methods, or if it is transcribed from DNA which has been altered or produced by non-natural, synthetic methods. The isolated nucleic acid may also be produced by the synthetic re-arrangement ("shuffling") of a part or parts of one or more allelic forms of the gene of interest. Likewise, a naturally-occurring nucleic acid (e.g., a promoter) becomes isolated if it is introduced to a different locus of the genome. Nucleic acids which are "isolated," as defined herein, are also referred to as "heterologous" nucleic acids.

Methods for isolation of promoter regions are well known in the art. One method is described in U.S. patent application Ser. No. 06/098,690 filed Aug. 31, 1998, herein incorporated by reference.

The sequence for the promoter region of the present invention is set forth in SEQ ID NO 1.

The promoter region of the invention may be isolated from any plant, including, but not limited to maize (*Zea mays*), canola (*Brassica napus, Brassica rapa ssp.*), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanut (*Arachis hypogaea*), cotton (*Gossypium hirsutum*), sweet potato (Ipomoea batatus), cassava (*Manihot esculenta*), coffee (*Cofea spp.*), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), oat (*Avena sativa*), vegetables, ornamentals, and conifers. Preferably, plants include maize, soybean, sunflower, safflower, canola, wheat, rye, alfalfa, and sorghum.

Promoter sequences from other plants may be isolated according to well-known techniques based on their sequence homology to the promoter sequence set forth herein. In these techniques, all or part of the known promoter sequence is used as a probe which selectively hybridizes to other sequences present in a population of cloned genomic DNA fragments (i.e. genomic libraries) from a chosen organism. Methods are readily available in the art for the hybridization of nucleic acid sequences.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al., eds., (1990) *PCR Protocols, A Guide to Methods and Applications, Academic Press*).

The terms "stringent conditions" or "stringent hybridization conditions" includes reference to conditions under which a probe will hybridize to its target sequence, to a detectably greater degree than to other sequences (e.g., at least 2-fold over background). Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Generally, probes of this type are in a range of about 1000 nucleotides in length to about 250 nucleotides in length.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995). See also Sambrook et al. (1989) *Molecular Cloning: A Laboratory Manual* (2nd ed. Cold Spring Harbor Laboratory, Cold Spring Harbor, N.Y.).

In general, sequences that correspond to the promoter sequence of the present invention and hybridize to the promoter sequence disclosed herein will be at least 50% homologous, 70% homologous, and even 85% homologous or more with the disclosed sequence. That is, the sequence similarity between probe and target may range, sharing at least about 50%, about 70%, and even about 85% sequence similarity.

Specificity is typically the function of post-hybridization washes, the critical factors being the ionic strength and temperature of the final wash solution. Generally, stringent wash temperature conditions are selected to be about 5° C. to about 2° C. lower than the melting point ($T_m$) for the specific sequence at a defined ionic strength and pH. The melting point, or denaturation, of DNA occurs over a narrow temperature range and represents the disruption of the double helix into its complementary single strands. The process is described by the temperature of the midpoint of transition, $T_m$, which is also called the melting temperature. Formulas are available in the art for the determination of melting temperatures.

Preferred hybridization conditions for the promoter sequence of the invention include hybridization at 42° C. in 50%(w/v) formamide, 6×SSC, 0.5%(w/v) SDS, 100 µg/ml salmon sperm DNA. Exemplary low stringency washing conditions include hybridization at 42° C. in a solution of 2×SSC, 0.5%(w/v) SDS for 30 minutes and repeating. Exemplary moderate stringency conditions include a wash in 2×SSC, 0.5%(w/v) SDS at 50° C. for 30 minutes and repeating. Exemplary high stringency conditions include a wash in 2×SSC, 0.5%(w/v) SDS, at 65° C. for 30 minutes and repeating. Sequences that correspond to the promoter of the present invention may be obtained using all the above conditions. For purposes of defining the invention, the high stringency conditions are used.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, CABIOS 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). BLAST (Basic Local Alignment Search Tool) is described by Altschul, S. F., et al., (1993) *J. Mol. Biol.* 215:403–410; see also www.ncbi.nlm.nih.gov/BLAST/.

Identity to the sequence of the present invention would mean a polynucleotide sequence having at least 65% sequence identity, more preferably at least 70% sequence identity, more preferably at least 75% sequence identity, more preferably at least 80% identity, more preferably at least 85% sequence identity, more preferably at least 90% sequence identity and most preferably at least 95% sequence identity wherein the percent sequence identity is based on the entire promoter region.

Sequence fragments with high percent identity to the sequence of the present invention also refer to those fragments of a particular promoter nucleotide sequence disclosed herein that operate to promote the seed-preferred expression of an operably linked heterologous nucleotide sequence. These fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments can be obtained by use of restriction enzymes to cleave the naturally occurring promoter nucleotide sequences disclosed herein; by synthesizing a nucleotide sequence from the naturally occurring promoter DNA sequence; or can be obtained through the use of PCR technology. See particularly, Mullis et al. (1987) *Methods Enzymol.* 155:335–350, and Erlich, ed. (1989) *PCR Technology* (Stockton Press, New York). Again, variants of these promoter fragments, such as those resulting from site-directed mutagenesis, are encompassed by the compositions of the present invention.

Nucleotide sequences comprising at least about 20 contiguous sequences of the sequence set forth in SEQ ID NO 1 are encompassed. These sequences can be isolated by hybridization, PCR, and the like. Such sequences encompass fragments capable of driving seed-preferred expression, fragments useful as probes to identify similar sequences, as well as elements responsible for temporal or tissue specificity.

Biologically active variants of the promoter sequence are also encompassed by the composition of the present invention. A regulatory "variant" is a modified form of a regulatory sequence wherein one or more bases have been modified, removed or added. For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digestion of a clone with this enzyme produces unidirectional nested deletions.

One example of a regulatory sequence variant is a promoter formed by one or more deletions from a larger promoter. The 5' portion of a promoter up to the TATA box near the transcription start site can be deleted without abolishing promoter activity, as described by Zhu et al., *The Plant Cell* 7: 1681–89 (1995). Such variants should retain promoter activity, particularly the ability to drive expression in seed or seed tissues. Biologically active variants include, for example, the native promoter sequences of the invention having one or more nucleotide substitutions, deletions or insertions. Promoter activity can be measured by Northern blot analysis, reporter activity measurements when using transcriptional fusions, and the like. See, for example, Sambrook et al. (1989) *Molecular Cloning: A Laboratory Manual* (2nd ed. Cold Spring Harbor Laboratory, Cold Spring Harbor, N.Y.), herein incorporated by reference.

The nucleotide sequence for the promoter of the invention, as well as fragments and variants thereof, can be provided in expression cassettes along with heterologous nucleotide sequences for expression in the plant of interest, more particularly in the seed of the plant. Such an expression cassette is provided with a plurality of restriction sites for insertion of the nucleotide sequence to be under the transcriptional regulation of the promoter. These expression cassettes are useful in the genetic manipulation of any plant to achieve a desired phenotypic response.

The genes of interest expressed by the promoter of the invention can be used for varying the phenotype of seeds. This can be achieved by increasing expression of endogenous or exogenous products in seeds. Alternatively, the results can be achieved by providing for a reduction of expression of one or more endogenous products, particularly enzymes or cofactors in the seed. These modifications result in a change in phenotype of the transformed seed.

General categories of genes of interest for the purposes of the present invention include, for example, those genes involved in information, such as Zinc fingers, those involved in communication, such as kinases, and those involved in housekeeping, such as heat shock proteins. More specific categories of transgenes include genes encoding important traits for agronomic quality, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms. It is recognized that any gene of interest, including the native coding sequence, can be operably linked to the promoter of the invention and expressed in the seed.

Modifications that affect grain traits include altering the levels of saturated and unsaturated fatty acids. Likewise, increasing the levels of lysine- and sulfur-containing amino acids may be desired, as well as modifications of the amount and/or type of starch contained in the seed. Examples of hordothionin protein modifications are described in PCT/US94/382 filed Apr. 10, 1997; PCT/US96/08219 filed Mar.26, 1997; PCT/US96/08220 filed Mar. 26, 1997 and U.S. Pat. No. 5,703,409 issued Dec. 30, 1997; the disclosures of which are incorporated herein by reference. Additional examples are lysine- and/or sulfur-rich seed protein encoded by the soybean 2S albumin described in PCT/US97/04409 filed Mar. 20, 1996, and the chymotrypsin inhibitor from barley, Williamson et al. (1987) *Eur. J. Biochem.* 165:99–106, the disclosures of which are incorporated by reference.

In a more preferred embodiment, the promoter of the instant invention modulates genes encoding proteins which act as cell cycle regulators, or which control carbohydrate metabolism or phytohormone levels, as has been shown in tobacco and canola with other tissue-preferred promoters. (Ma, Q. H., et al., (1998) *Australian Journal of Plant Physiology* 25(1): 53–59; Roeckel, P., et al., (1997) *Transgenic Research* 6(2):133–141.) Expression of endogenous or heterologous nucleotides under the direction of the promoter may result in maintenance of a desirable seed phenotype that might otherwise be altered under adverse environmental conditions.

Derivatives of the following genes can be made by site-directed mutagenesis to increase the level of preselected amino acids in the encoded polypeptide. For example, the gene encoding the barley high lysine polypeptide (BHL), is derived from barley chymotrypsin inhibitor, PCT/US97/20441 filed Nov. 1, 1996 and PCT/US97/20441 filed Oct. 31, 1997; the disclosures of each are incorporated herein by reference. Other proteins include methionine-rich plant proteins such as from sunflower seed, Lilley et al. (1989) *Proceedings of the World Congress on Vegetable Protein Utilization in Human Foods and Animal Feedstuffs,* Applewhite, H. (ed.); American Oil Chemists Soc., Champaign, IL:497–502, incorporated herein by reference; corn, Pedersen et al. (1986) *J. Biol. Chem.* 261:6279; Kirihara et al. (1988) *Gene* 71:359, both incorporated herein by reference; and rice, Musumura et al. (1989) *Plant Mol. Biol.* 12:123, incorporated herein by reference. Other important genes encode latex, Floury 2, growth factors, seed storage factors and transcription factors.

Agronomic traits in seeds can be improved by altering expression of genes that affect the response of seed growth and development during environmental stress, Cheikh-N et al., (1994) *Plant Physiol.* 106(1):45–51, and genes controlling carbohydrate metabolism to reduce seed abortion in maize, Zinselmeier et al. (1995) *Plant Physiol.* 107(2):385–391.

Insect resistance genes may encode resistance to pests that have great yield drag such as rootworm, cutworm, European Corn Borer, and the like. Such genes include, for example, *Bacillus thuringiensis* endotoxin genes, U.S. Pat. Nos. 5,366,892; 5,747,450; 5,737,514; 5,723,756; 5,593,881; Geiser et al. (1986) Gene 48:109; lectins, Van Damme et al. (1994) *Plant Mol. Biol.* 24:825; and the like.

Genes encoding disease resistance traits include detoxification genes, such as against fumonosin (PCT/US95/10284 filed Jun. 7, 1995); avirulence (avr) and disease resistance (R) genes Jones et al. (1994) *Science* 266:789; Martin et al. (1993) *Science* 262:1432; Mindrinos et al. (1994) *Cell* 78:1089; and the like.

Alterations in gene expression may also affect the type or amount of products of commercial interest; for example, starch for the production of paper, textiles and ethanol. Another important commercial use of transformed plants is the production of polymers and bioplastics such as described in U.S. Pat. No. 5,602,321 issued Feb. 11, 1997. Genes such as B-Ketothiolase, PHBase (polyhydroxybutyrate synthase) and acetoacetyl-CoA reductase (see Schubert et al. (1988) *J. Bacteriol* 170(12):5837–5847) facilitate expression of polyhyroxyalkanoates (PHAs).

The nucleotide sequence operably linked to the promoter disclosed herein can be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the promoter sequence disclosed herein can be operably linked to antisense DNA sequences to reduce or inhibit expression of a native protein in the plant seed.

The expression cassette will also include at the 3' terminus of the heterologous nucleotide sequence of interest, a transcriptional and translational termination region functional in plants. The termination region can be native with the promoter nucleotide sequence of the present invention, can be native with the DNA sequence of interest, or can be derived from another source. Convenient termination regions are available from the Ti-plasmid of *A. tumefaciens,* such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. (1989) *Proc. Nat. Acad. Sci. USA* 86:6126–6130; potyvirus leaders, for example, TEV leader (Tobacco Etch Virus), Allison et al. (1986); MDMV leader (Maize Dwarf Mosaic Virus), *Virology* 154:9–20; human immunoglobulin heavy-chain binding protein (BiP), Macejak et al. (1991) *Nature*

353:90–94; untranslated leader from the coat protein mRNA of alfalfa mosaic virus (AMV RNA 4), Jobling et al. (1987) *Nature* 325:622–625); tobacco mosaic virus leader (TMV), Gallie et al. (1989) *Molecular Biology* of RNA, pages 237–256; and maize chlorotic mottle virus leader (MCMV) Lommel et al. (1991) *Virology* 81:382–385. See also Della-Cioppa et al. (1987) *Plant Physiology* 84:965–968. The cassette can also contain sequences that enhance translation and/or mRNA stability such as introns.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

As noted herein, the present invention provides vectors capable of expressing genes of interest under the control of the promoter. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector comprising the promoter sequence of the present invention operably linked to a heterologous nucleotide sequence in an expression cassette, can also contain at least one additional nucleotide sequence for a gene to be cotransformed into the organism. Alternatively, the additional sequence(s) can be provided on another transformation vector.

Vectors that are functional in plants can be binary plasmids derived from Agrobacterium. Such vectors are capable of transforming plant cells. These vectors contain left and right border sequences that are required for integration into the host (plant) chromosome. At minimum, between these border sequences is the gene to be expressed under control of the promoter. In preferred embodiments, a selectable marker and a reporter gene are also included. For ease of obtaining sufficient quantities of vector, a bacterial origin that allows replication in *E. coli* is preferred.

Reporter genes can be included in the transformation vectors. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol. Cell. Biol.* 7:725–737; Goff et al. (1990) *EMBO J.* 9:2517–2522; Kain et al. (1995) *BioTechniques* 19:650–655; and Chiu et al. (1996) *Current Biology* 6:325–330.

Selectable marker genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. (1983) *EMBO J.* 2:987–992; methotrexate, Herrera Estrella et al. (1983) *Nature* 303:209–213; Meijer et al. (1991) *Plant Mol. Biol.* 16:807–820; hygromycin, Waldron et al. (1985) *Plant Mol. Biol.* 5:103–108; Zhijian et al. (1995) *Plant Science* 108:219–227; streptomycin, Jones et al. (1987) *Mol. Gen. Genet.* 210:86–91; spectinomycin, Bretagne-Sagnard et al. (1996) *Transgenic Res.* 5:131–137; bleomycin, Hille et al. (1990) *Plant Mol. Biol.* 7:171–176; sulfonamide, Guerineau et al. (1990) *Plant Mol. Biol.* 15:127–136; bromoxynil, Stalker et al. (1988) *Science* 242:419–423; glyphosate, Shaw et al. (1986) *Science* 233:478–481; phosphinothricin, DeBlock et al. (1987) *EMBO J.* 6:2513–2518.

Other genes that could serve utility in the recovery of transgenic events but might not be required in the final product would include, but are not limited to, examples such as GUS (β-glucuronidase), Jefferson (1987) *Plant Mol. Biol. Rep.* 5:387); GFP (green florescence protein), Chalfie et al. (1994) *Science* 263:802; luciferase, Teeri et al. (1989) *EMBO J.* 8:343; and the maize genes encoding for anthocyanin production, Ludwig et al. (1990) *Science* 247:449.

The transformation vector comprising the particular promoter sequence of the present invention, operably linked to a heterologous nucleotide sequence of interest in an expression cassette, can be used to transform any plant. In this manner, genetically modified plants, plant cells, plant tissue, seed, and the like can be obtained. Transformation protocols can vary depending on the type of plant or plant cell, i.e., monocot or dicot, targeted for transformation. Suitable methods of transforming plant cells include microinjection, Crossway et al. (1986) *Biotechniques* 4:320–334; electroporation, Riggs et al. (1986) *Proc. Natl. Acad. Sci. USA* 83:5602–5606; Agrobacterium-mediated transformation, see for example, Townsend et al. U.S. Pat. No. 5,563,055; direct gene transfer, Paszkowski et al. (1984) *EMBO J.* 3:2717–2722; and ballistic particle acceleration, see for example, Sanford et al. U.S. Pat. No. 4,945,050; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923–926. Also see Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Datta et al. (1990) *Biotechnology* 8:736–740 (rice); Klein et al. (1988) *Proc. Natl. Acad. Sci. USA* 85:43054309 (maize); Klein et al. (1988) *Biotechnology* 6:559–563 (maize); Klein et al. (1988) *Plant Physiol.* 91:440444 (maize); Fromm et al. (1990) *Biotechnology* 8:833–839; Hooydaas-Van Slogteren et al. (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. G. P. Chapman et al. (Longman, New York), pp. 197–209 (pollen); Kaeppler et al. (1990) *Plant Cell Reports* 9:415–418; and Kaeppler et al. (1992) *Theor. Appl. Genet.* 84:560–566 (whisker-mediated transformation); D. Halluin et al. (1992) *Plant Cell* 4:1495–1505 (electroporation); Li et al. (1993) *Plant Cell Reports* 12:250–255 and Christou et al. (1995) *Annals of Botany* 75:407413 (rice); Osjoda et al. (1996) *Nature Biotechnology* 14:745–750 (maize via Agrobacterium tumefaciens); all of which are herein incorporated by reference.

The cells that have been transformed can be grown into plants in accordance with conventional ways. See, for example, McCormick et al. (1986) *Plant Cell Reports* 5:81–84. These plants can then be grown, and pollinated with the same transformed strain or different strains. The resulting hybrid having seed-preferred expression of the desired phenotypic characteristic can then be identified. Two or more generations can be grown to ensure that seed-preferred expression of the desired phenotypic characteristic is stably maintained and inherited.

The following examples are offered by way of illustration and not by way of limitation.

EXAMPLES

The promoter region for a maize gene homologous to the barley pZE40 gene was isolated and cloned and its expression tested as described below.

Example 1
Isolation of the mZE40-2 Promoter:

A maize ortholog to the barley pZE40 gene (Smith, L. M., et al.; Plant Mol. Biol. 20:255–266 (1992)) was identified in a Pioneer Hi-Bred International proprietary database. Three primers were designed based on the ortholog sequence:

SEQ ID No. 2: GCCGCAGCMGACATGCTTTGAT-GAGTC;

SEQ ID No. 3: GCGGTCTCCACGTCAGGGAA-CATCTT;

SEQ ID No. 4: TTGCCGCCGCAGCAAGACATGCTTT.

The primers and B73 maize genomic DNA were used in conjunction with the GenomeWalker Kit™ (Clontech) to isolate the promoter. The manufacturer's protocol was followed and approximately 2.9 Kb of 5' sequence were obtained. Analysis of the upstream sequence revealed no obvious control element motifs. An approximately 1.6 Kb fragment of the 5' upstream sequence, starting at the first methionine based on the barley sequence, was then isolated. Two primers (SEQ ID No. 5: CCCMGCTTAGTTATGGCG-GTACTACCTATCATCTAG and SEQ ID No. 6: CGGGATCCCGGCTTTGATGAGTCGAAGGAA) with restriction sites were designed and PCR was used to isolate the promoter fragment using techniques known to those of skill in the art. The promoter fragment was then inserted into a transformation vector (see Example 2, below). The construct was transformed into maize and the plants were used to evaluate promoter activity. The fragment was 1626 bp long (Sequence I.D. No.: 1) and was designated mZE40-2.

Example 2
Expression of the mZE40-2 Promoter:

The Agrobacterium strain utilized in this example was modified to contain nucleic acid encoding the mZE40-2 promoter and a GUS reporter gene to be expressed in the transformed cells. The nucleic acid to be transferred is incorporated into the T-region and is flanked by at least one T-DNA border sequence.

In the Ti plasmid, the T-region is distinct from the vir region whose functions are responsible for transfer and integration. Binary vector systems have been developed where the manipulated disarmed T-DNA carrying foreign DNA and the vir functions are present on separate plasmids. In this manner, a modified T-DNA region comprising foreign DNA (the nucleic acid to be transferred) is constructed in a small plasmid which replicates in *E. coli*. This plasmid is transferred conjugatively in a tri-parental mating into *A. tumefaciens* which contains a compatible plasmid-carrying virulence gene. The vir functions are supplied in trans to transfer the T-DNA into the plant genome.

Preferred vectors are super-binary vectors. See, for example, U.S. Pat. No. 5,591,616 and EPA 0604662A1, herein incorporated by reference. Such a super-binary vector has been constructed containing a DNA region originating from the virulence region of Ti plasmid pTiBo542 (Jin et al. (1987) *J. Bacteriol.* 169:4417–4425) contained in a super-virulent *Agrobacterium tumefaciens* A281 exhibiting extremely high transformation efficiency (Hood et al. (1984) *Biotechnol.* 2:702–709; Hood et al. (1986) *J. Bacteriol.* 168:1283–1290; Komari et al. (1986) *J. Bacteriol.* 166:88–94; Jin et al. (1987) *J. Bacteriol.* 169:4417–4425; Komari T. (1989) *Plant Science* 60:223–229; ATCC Accession No. 37394).

Super-binary vectors are known in the art and include pTOK162 (Japanese Patent Appl. (Kokai) No. 4-222527, EP-A-504,869, EP-A-604,662, and U.S. Pat. No. 5,591,616 herein incorporated by reference) and pTOK233 (Komari, T. (1990) *Plant Cell Reports* 9:303–306; and Ishida et al. (1996) *Nature Biotechnology* 14:745; herein incorporated by reference). Other super-binary vectors may be constructed by the methods set forth in the above references. For example, super-binary vector pTOK162 is capable of replication in both *E. coli* and in *A. tumefaciens*. Additionally, the vector contains the virB, virC, and virG genes from the virulence region of pTiBo542. The plasmid also contains an antibiotic resistance gene, a selectable marker gene, and the nucleic acid of interest to be transformed into the plant.

The T-region of the super-binary vectors and other vectors for use in gene expression are constructed to have restriction sites for the insertion of the genes to be delivered. Alternatively, the DNA to be transformed can be inserted in the T-DNA region of the vector by utilizing in vivo homologous recombination. See, Herrera-Esterella et al. (1983) *EMBO J.* 2:987–995; Horch et al. (1984) *Science* 223:496–498). Such homologous recombination relies on the fact that the super-binary vector has a region homologous with a region of pBR322 or other similar plasmid. Thus, when the two plasmids are brought together a desired gene is inserted into the super-binary vector by genetic recombination via the homologous regions.

The vectors of this example were constructed using standard molecular biology techniques known to those of ordinary skill in the art. A reporter gene and a selectable marker gene were inserted between the T-DNA borders of a super-binary vector. The reporter gene was the β-glucuronidase (GUS) gene (Jefferson, R. A. et al., 1986, *Proc. Natl. Acad. Sci.* (*USA*) 83:8447–8451) into whose coding region was inserted the second intron from the potato ST-LS1 gene (Vancanneyt et al., *Mol. Gen. Genet.* 220:245–250, 1990), to produce intron-GUS, in order to prevent expression of the gene in Agrobacterium (see Ohta, S. et al., 1990, *Plant Cell Physiol.* 31(6):805–813). A fragment containing bases 2 to 310 from the terminator of the potato proteinase inhibitor (pinII) gene (An et al., *Plant Cell* 1:115–122, 1989) was blunt-end ligated downstream of the GUS coding sequence, to create the GUS expression cassette.

For the selectable marker, a Cauliflower Mosaic Virus 35S promoter with a duplicated enhancer region (2×35S; bases −421 to −90 and −421 to +2 from Gardner et al., *Nucl. Acids Res.* 9:2871–2888, 1981) was created. A fragment containing Omega-prime leader sequence (Gallie, D. R., et al., 1987, *Nucleic Acids Research* 15(8):3257–3273) was inserted downstream of the 35S promoter followed by a fragment containing the first intron of the maize alcohol dehydrogenase gene ADH1-S (Dennis et al., *Nucl. Acids Res.* 12:3983–3990, 1984). The BAR coding sequence (Thompson et al., *EMBO J.* 6:2519–2523, 1987) was cloned downstream of the leader sequence, with the pinII terminator ligated downstream of BAR, to create the BAR expression cassette.

In summary, the plasmid was constructed by inserting the GUS expression cassette and the BAR expression cassette between the right and left T-DNA borders in pSB11. The GUS cassette is inserted proximal to the right T-DNA border. The mZE40-2 promoter fragment was inserted into the vector in front of the intron-GUS gene. The plasmid pSB11 was obtained from Japan Tobacco Inc. (Tokyo, Japan). The construction of pSB11 from pSB21 and the construction of pSB21 from starting vectors is described by Komari et al. (1996, Plant J. 10:165–174). The T-DNA of this plasmid was integrated into the superbinary plasmid pSB1 (Saito et al., EP 672 752 A1) by homologous recombination between the two plasmids. The plasmid pSB1 was also obtained from Japan Tobacco Inc. *E. coli* strain HB101 containing the plasmid containing the mZE40-2 promoter was mated with Agrobacterium strain LBA4404 harboring pSB1 to create the cointegrate plasmid in the *Agrobacterium tumefaciens* strain LBA4404 using the method of Ditta et al., (*Proc. Natl. Acad. Sci. USA* 77:7347–7351,1980). (See also, U.S. patent application Ser. No. 08/788,018, WO Publication No. 98/32326, for a further discussion of Agrobacterium-mediated transformation, herein incorporated by reference.)

The resulting co-integrated plasmid, the product from the tri-parental mating described above, was transformed into the genotypes (1) Hi-II and (2) Hi-II x PHN46. (See U.S. Pat. No. 5,567,861 for more information about PHN46.) T0 plants were generated and promoter analysis was conducted on T1 seed from both genotypes.

Immature seeds from 26 transgenic events were collected at specific intervals after pollination, starting at 2 days after pollination (DAP) and extending to physiological maturity. Each seed was dissected vertically from silk scar to pedicel and was examined by histochemical staining. Specifically, each section was incubated in a solution of 0.1 M sodium phosphate buffer, pH 7.0, containing 0.5% X-gluc (5-bromo-4-chloro-3-indolyl-β-D-glucuronic acid, sodium salt, dissolved in DMSO first) and 0.1% Triton X-100. Sections were incubated overnight at 37° C., but in some cases, sections were extensively stained within 2 to 3 hours.

Most events expressed GUS very strongly in carpel or pericarp and pedicel prior to 10 DAP. Between 10 and 15 DAP expression was mostly localized to the aleurone and then at about 15 to 20 DAP, GUS staining was also observed on the scutellum side of the embryo. The aleurone and scutellum expression is consistent with that observed in barley, with the barley gene. In addition to harvesting developing seeds, silks, husks, leaves, tassels and roots were also collected. Variable expression was observed in leaves and roots of some events. The tissue and temporal specificity of the promoter was confirmed in the T2 generation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications can be practiced within the scope of the appended claims.

Deposit

Plasmids containing polynucleotide sequences of the invention were deposited on Jun. 13, 2000, with the American Type Culture Collection (ATCC), 10801 University Boulevard, Manassas, Va. USA, 20110-2209, and assigned Accession No. PTA-2022. This deposit will be maintained under the terms of the Budapest Treaty on the International Recognition of the Deposit of Microorganisms for the Purposes of Patent Procedure. In addition, during the pendency of this patent application, access to the deposited cultures will be available to the Commissioner of Patents and Trademarks and to persons determined by the Commissioner to be entitled thereto under 37 C.F.R. §114 and 35 U.S.C. §122.

This deposit was made merely as a convenience for those of skill in the art and is not an admission that a deposit is required under 35 U.S.C. §112. All restrictions imposed by the depositor on the availability to the public of the deposited material will be irrevocably removed upon granting of a patent. However, it should be understood that the availability of a deposit does not constitute a license to practice the subject invention in derogation of patent rights granted by government action.

That which is claimed is:

1. An isolated promoter that is capable of driving transcription in a seed-preferred manner, wherein said promoter comprises a polynucleotide of SEQ ID NO 1.

2. A polynucleotide of claim 1 isolated from maize.

3. An expression cassette comprising a promoter of claim 1 and a nucleotide sequence operably linked to said promoter, wherein said promoter is capable of initiating transcription and expression of said nucleotide sequence in a seed of a plant transformed with said expression cassette.

4. A transformation vector comprising an expression cassette of claim 3.

5. A plant, or its parts, stably transformed with an expression cassette of claim 3.

6. The plant parts of claim 5, wherein the plant parts are selected from the group consisting of: cells, protoplasts, cell tissue cultures, callus, cell clumps, embryos, pollen, ovules, seeds, flowers, kernels, ears, cobs, leaves, husks, stalks, roots, root tips, anthers, and silk.

7. The plant of claim 5, wherein said plant is a monocot.

8. The plant of claim 7, wherein said monocot is maize, barley, wheat, oat, rye, sorghum or rice.

9. The plant of claim 5, wherein said plant is a dicot.

10. The plant of claim 9, wherein said dicot is soybean, alfalfa, safflower, tobacco, sunflower, cotton, or canola.

11. Seeds of the plant of claim 5 comprising within their genome said expression cassette.

12. A method for selectively expressing a first nucleotide sequence in a plant seed, said method comprising transforming a plant with a transformation vector comprising an expression cassette, said expression cassette comprising a promoter and a first nucleotide sequence operably linked to said promoter, wherein said promoter is capable of initiating transcription and expression of said first nucleotide sequence in a plant seed, wherein said promoter comprises a second nucleotide sequence comprising SEQ ID NO 1.

13. The method of claim 12, wherein said first nucleotide sequence encodes a polypeptide involved in fatty acid metabolism.

14. The method of claim 12, wherein said first nucleotide sequence encodes a polypeptide involved in protein metabolism.

15. The method of claim 12, wherein said first nucleotide sequence encodes a polypeptide involved in carbohydrate metabolism.

16. The method of claim 12, wherein said first nucleotide sequence encodes a polypeptide involved in phytohormone biosynthesis.

17. The method of claim 12, wherein said first nucleotide sequence encodes a polypeptide involved in cell cycle regulation.

* * * * *

SEQUENCE LISTING

<160> NUMBER OF SEQ ID NOS: 6

<210> SEQ ID NO 1
<211> LENGTH: 1626
<212> TYPE: DNA
<213> ORGANISM: Zea mays
<220> FEATURE:
<221> NAME/KEY: promoter
<222> LOCATION: (1)...(1626)

<400> SEQUENCE: 1

```
aagcttagct agatcatttg taagaatgca acttgttcat atagcatggc t acagcctac    60 atcatctgaa atagacctgt ttataggata cctaagctca attcaccta t atctaaaac    120 ctacgaggcc taaacacacc cgtcctcaag aaaacgacca aaccaaacca a accatgcgt    180 ccgtgtcatg gttttgtaga cacgtttacg tatcaattat agtgttctga t tttttatat    240
```

-continued

```
tctcctaatt atttagagct aaatttattt ttatgatagc agagatctaa a tattttgt      300 tttgattttt tatatactaa aatcatctct acaatattag agattttaaa t gctcagaag    360 aattttactt gaattaaaac ctttactgat ttttaactaa aacggagacc a aaagaaatc    420 tatccaaggc tgcctctaag agccttcgtg tctcgttttc ttatttcaga c ttcactcat    480 cttcttattt caggctccac tatataaggt ggtctctagt atctttccta t cacatatcc    540 tatttaaaac tttagtatat aaacattat aattcataat ataaatcgat t attttacac    600 gatctcagcc taaaagcggt aatatgcacg ctctgagcat ggcccaagct c cacgttaac    660 cgttctgtca aaaaaaaaaa catctagtct agaatggaaa acacacgatt t tagaagtta   720 ggactagttt ggcaactcaa ttttccaaat gattctcatt cttttaagag g atttaattt   780 attttttggt aaaataggaa tcactagaaa ctctattttt tcaagagaaa g taagctatt   840 tttttagaaa aataaaaaat cccttaaaaa atattgttcg taaattagcc c taagatgga   900 ctaaaaatct ggttttatag aatagggagg gatcgagcaa ccgccaaatc t acgcgccaa   960 aaggtacct tttccgtgaa taaacacgac tgcggcgatc acgatctgat c gaactcgta  1020 gaataaaatg gagcagcgga atagtgtggg aggcacaagc acaggaggag c tgaaaccga  1080 accgaagtgg cgaacacgat ccccactccg gccggcaccc gagtgtgcga g acgtgtggg  1140 gctgatctga cgagcctgga agaagaagaa gaaaaaaaag tcctcacgct c ctgcttggc  1200 tccatcgaca gctcactagc tgctaccgga tgctcgcgtc tctgatgcct c tcgattcat  1260 catccatcgt tggtggcggc ggcggggcgg caaaggttct gattccgcag c agccaagtg  1320 ctcctcctgc agacgaaaat gacggcagag gttggcgttg atccaggaga c tcatcagtt  1380 tagtttaata atgaatctgt agcaggcgct tcagtctctc atcggatgag c gagcagctt  1440 agcagagcag gtggtggtcc ctggctcgcc cccgtccatt cttttcccgcc c gtcctgccg  1500 tccactccgc cgcctattta taccctcct cgcccaccct gccatcctca c catcgcaat  1560 tcacaagcaa agcaatcaga gccaagcacc caccgtcctc ctttctttcc t tcgactcat  1620 caaagc                                                               1626
```

<210> SEQ ID NO 2
<211> LENGTH: 28
<212> TYPE: DNA
<213> ORGANISM: Zea mays

<400> SEQUENCE: 2

```
gccgcagcaa gacatgcttt gatgagtc                                         28
```

<210> SEQ ID NO 3
<211> LENGTH: 26
<212> TYPE: DNA
<213> ORGANISM: Zea mays

<400> SEQUENCE: 3

```
gcggtctcca cgtcagggaa catctt                                           26
```

<210> SEQ ID NO 4
<211> LENGTH: 25
<212> TYPE: DNA
<213> ORGANISM: Zea mays

<400> SEQUENCE: 4

```
ttgccgccgc agcaagacat gcttt                                            25
```

```
<210> SEQ ID NO 5
<211> LENGTH: 37
<212> TYPE: DNA
<213> ORGANISM: Zea mays

<400> SEQUENCE: 5
cccaagctta gttatggcgg tactacctat catctag                              37

<210> SEQ ID NO 6
<211> LENGTH: 30
<212> TYPE: DNA
<213> ORGANISM: Zea mays

<400> SEQUENCE: 6
cgggatcccg gctttgatga gtcgaaggaa                                      30
```